(12) United States Patent
Abo et al.

(10) Patent No.: US 11,077,042 B2
(45) Date of Patent: Aug. 3, 2021

(54) LIQUID HAIR DYE COMPOSITION

(71) Applicant: KAO CORPORATION, Tokyo (JP)

(72) Inventors: Fumina Abo, Sumida-ku (JP); Shunsuke Watanabe, Arakawa-ku (JP); Keiji Monda, Katsusika-ku (JP); Takeshi Iizaki, Saitama (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 16/648,989

(22) PCT Filed: Sep. 20, 2018

(86) PCT No.: PCT/JP2018/034742
§ 371 (c)(1),
(2) Date: Mar. 19, 2020

(87) PCT Pub. No.: WO2019/059253
PCT Pub. Date: Mar. 28, 2019

(65) Prior Publication Data
US 2020/0281832 A1  Sep. 10, 2020

(30) Foreign Application Priority Data

Sep. 20, 2017 (JP) .............................. JP2017-180759

(51) Int. Cl.
| | |
|---|---|
| *A61Q 5/10* | (2006.01) |
| *A61K 8/49* | (2006.01) |
| *A61K 8/19* | (2006.01) |
| *A61K 8/22* | (2006.01) |
| *A61K 8/34* | (2006.01) |
| *A61K 8/41* | (2006.01) |

(52) U.S. Cl.
CPC .................. *A61K 8/49* (2013.01); *A61K 8/19* (2013.01); *A61K 8/22* (2013.01); *A61K 8/34* (2013.01); *A61K 8/41* (2013.01); *A61K 8/415* (2013.01); *A61Q 5/10* (2013.01); *A61K 2800/432* (2013.01); *A61K 2800/88* (2013.01)

(58) Field of Classification Search
CPC .......... A61Q 5/10; A61Q 5/065; A61K 8/411; A61K 8/22; A61K 8/49; A61K 8/19; A61K 8/41; A61K 2800/88; A61K 2800/882; A61K 8/34; A61K 8/23; A61K 2800/432
USPC ..................................................... 8/405, 437
See application file for complete search history.

(56) References Cited

U.S. PATENT DOCUMENTS

| 9,498,417 B2 | 11/2016 | Möhring et al. |
| 2004/0019982 A1 | 2/2004 | Pratt et al. |
| 2017/0196790 A1 | 7/2017 | Saimiya et al. |
| 2017/0196791 A1 * | 7/2017 | Nojiri ....................... A61K 8/43 |
| 2017/0258695 A1 | 9/2017 | Consoli et al. |
| 2018/0369103 A1 | 12/2018 | Owens et al. |

FOREIGN PATENT DOCUMENTS

| JP | 6-271435 A | 9/1994 |
| JP | 2002-97120 A | 4/2002 |
| JP | 2003-342139 A | 12/2003 |
| JP | 2005-139155 A | 6/2005 |
| JP | 2016-11298 A | 1/2016 |
| JP | 2019-055945 A | 4/2019 |
| JP | 2019-55947 A | 4/2019 |
| JP | 2019-151615 A | 9/2019 |
| JP | 2019-151616 A | 9/2019 |
| WO | WO 2015/186817 A1 * | 12/2015 ............... A61Q 5/10 |
| WO | WO 2016/093189 A1 | 6/2016 |
| WO | WO 2017/082267 A1 | 5/2017 |

OTHER PUBLICATIONS

STIC Search Report dated Sep. 8, 2020.*
International Search Report dated Dec. 18, 2018 in PCT/JP2018/034742 filed on Sep. 20, 2018, 2 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A liquid hair dye composition comprising the following components (A) and (B), wherein
the content (X) of the component (A) in the composition is 1.5 mass % or more and 5.16 mass % or less,
the content (Y) of the component (B) in the composition is 9 mass % or more and 98.5 mass % or less,
the composition satisfies the following equation (1) (with a proviso that a composition in which the diol content is 50 mass % or more and the water content is 2 mass % or less in the liquid hair dye composition is excluded).

$$Y \geq 22.75X - 22.75 \qquad (1)$$

(A) an azo dye represented by the following formula (A-2)

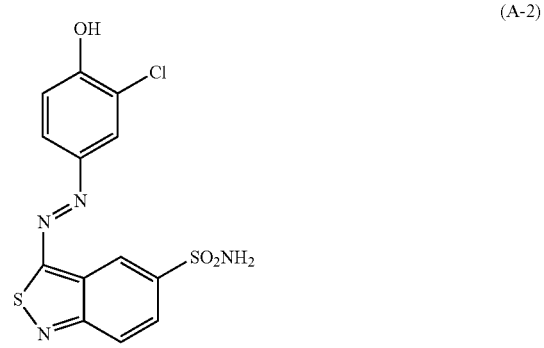

(B) a monoalcohol and/or a diol other than alkanolamines

12 Claims, No Drawings

LIQUID HAIR DYE COMPOSITION

FIELD OF THE INVENTION

The present invention relates to a liquid hair dye composition.

BACKGROUND OF THE INVENTION

Typical hair dye agents include a two-agent type permanent hair dye agent containing a first agent containing an alkaline agent and a second agent containing an oxidizing agent, and a one-agent type semipermanent hair dye agent containing at least one of direct dyes such as an acidic dye, a basic dye and a nitro dye. The direct dyes are widely used because some of them excellently exhibit a vivid color, and various forms such as liquid, cream, foam and powder exist (see e.g., PTLs 1 to 3).

(PTL 1) JP 2005-139155 A
(PTL 2) JP Hei 6-271435 A
(PTL 3) JP 2002-97120 A

SUMMARY OF THE INVENTION

The present invention provides a liquid hair dye composition comprising the following components (A) and (B), wherein
the content (X) of the component (A) in the composition is 1.5 mass % or more and 5.16 mass % or less,
the content (Y) of the component (B) in the composition is 9 mass or more and 98.5 mass % or less,
the composition satisfies the following equation (1) (with a proviso that a composition in which the diol content is 50 mass % or more and the water content is 2 mass or less in the liquid hair dye composition is excluded).

$$Y \geq 22.75X - 22.75 \quad (1)$$

(A) an azo dye represented by the following formula (A-2)

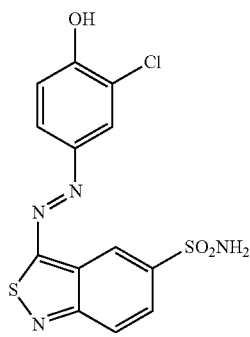

(A-2)

(B) a monoalcohol and/or a diol other than alkanolamines

DETAILED DESCRIPTION OF THE INVENTION

When a semipermanent hair dye agent as described above is prepared as a liquid composition, some direct dyes can be deposited during storage when contained in a high concentration, because they are not soluble enough in water or other solvents. Due to the low concentration of the direct dyes, hair dyeability can be impaired, or a color obtained as a result of hair dyeing can be different from an intended one.

As described above, a powder direct dye is known which is storable in an environment free from problems (e.g., deposition) caused by low solubility and brought into a mixture with a liquid preparation before use. However, mixing a powder hair dye composition sufficiently with a liquid preparation can involve such problems as requiring time, or requiring a large amount of the liquid preparation which decreases the dye concentration.

Because of this, the development of a liquid hair dye composition free from deposition of direct dyes during storage, regardless of containing a high concentration of direct dye, has been hoped for.

The present inventors found that hair can be dyed in two layers each having different hues only by applying the obtained mixture to hair, and found that an unprecedented effect of hair appearance having hue and color tone varying by difference in the viewing angle of the hair is exerted, when a hair dye composition containing a specific azo dye is mixed with a two-agent type permanent hair dye agent using an oxidation dye to dye hair. As such, it is also demanded that the liquid hair dye composition described above can be suitably applied to the aspect in which a specific azo dye is contained in a high concentration and the composition is mixed with a two-agent type permanent hair dye agent.

The present invention relates to a liquid hair dye composition which exhibits high dyeability even at a low amount because of a high concentration of direct dyes, and exhibits excellent miscibility with other preparations and thus facilitates color toning because, even if the other preparations contain other dyes, the liquid hair dye composition does not decrease the concentration of the dyes greatly.

As a result of earnest investigation, the present inventors found that a specific azo dye could be dissolved in a high concentration with stability by setting a fixed concentration relationship with a specific solvent, thereby completing the present invention.

[Component (A): Azo Dye]

The liquid hair dye composition of the present invention contain, as component (A), an azo dye represented by Formula (A-2) below (HC Blue 18). The pKa of the azo dye (A-2) is 6.0, and assumes blue color by proton dissociation.

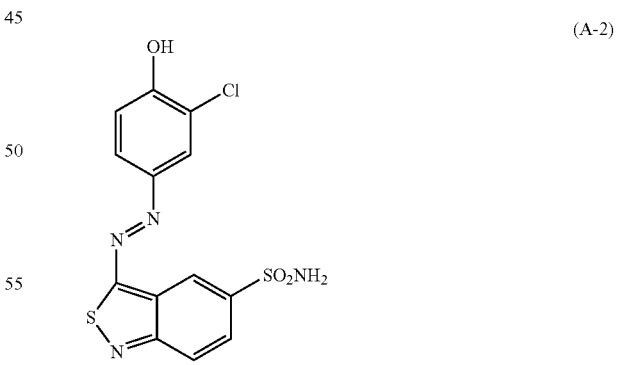

The content of the component (A) in the liquid hair dye composition of the present invention is 1.5 mass % or more, preferably 1.6 mass % or more, more preferably 1.7 mass % or more, even more preferably 1.8 mass % or more from the viewpoint of imparting sufficient hair dyeability even by using a small amount, and 5.16 mass % or less, preferably 5.0 mass % or less, more preferably 4.5 mass % or less, even more preferably 4.19 mass % or less, even more preferably 4.0% or less from the viewpoint of storage stability, and preferably 3.5 mass % or less, more preferably 3.41 mass % or less, even more preferably 3.0 mass % or less further considering economic efficiency.

[Component (B): Solvent]

The liquid hair dye composition of the present invention contains as component (B), a monoalcohol and/or a diol, other than alkanolamines. Preferable examples of the monoalcohol include, a lower alkanol such as ethanol, 1-propanol, and 2-propanol; an aromatic alcohol such as benzyl alcohol and 2-benzyloxyethanol; an alkoxy alcohol such as ethoxyethanol, ethoxy diglycol, and methoxyethanol. Preferable examples of the dialcohol include, propylene glycol, 1,3-butanediol, polyethylene glycol, and diethylene glycol. From the viewpoint of storage stability and change in hue or color tone of the appearance of the hair depending on the angle at which the hair is viewed, the component (B) preferably contains one or more species selected from the group consisting of a lower monoalcohol having 2 or 3 carbon atoms, a monocyclic aromatic monoalcohol, and a dial having 2 to 6 carbon atoms, more preferably one or more species selected from the group consisting of a monocyclic aromatic monoalcohol and a diol having 2 to 6 carbon atoms, and further preferably one or more species selected from diols having 2 to 6 carbon atoms. More specifically, from the above viewpoint, the composition preferably contains one or more species selected from the group consisting of ethanol, 1-propanol, 2-propanol, benzyl alcohol, 2-benzyloxyethanol, propylene glycol, 1,3-butanediol, and diethylene glycol, more preferably one or more species selected from the group consisting of benzyl alcohol, 2-benzyloxyethanol, propylene glycol, 1,3-butanediol, and diethylene glycol, further preferably one or more species selected from the group consisting of propylene glycol, 1,3-butanediol, and diethylene glycol, and even more preferably propylene glycol.

The content of the component (B) in the liquid hair dye composition of the present invention is 9 mass % or more, preferably 10 mass % or more, more preferably 12 mass % or more, more preferably 14 mass % or more, more preferably 16 mass % or more, and even more preferably 20 mass % or more from the viewpoint of obtaining good storage stability and uniform hair dyeability; the content of the component (B) in the liquid hair dye composition is 98.5% or less, preferably 97% or less, more preferably 95% or less, even more preferably 93% or less, even more preferably 90% or less, and even more preferably 85 mass % or less from the viewpoint of obtaining adequate hair dyeability.

From the liquid hair dye composition of the present invention, those having a diol content of 50 mass % or more and a water content of 2 mass % or less are excluded.

It is important that the content (X) of component (A) and the content (Y) of component (B) in the liquid hair dye composition satisfy the following equation (1) from the viewpoint of stably dissolving the component (A), $$Y \geq 22.75X - 22.75 \quad (1)$$

It is further preferable that the above X and Y satisfy the following equation (1a) and moreover the equation (1b) from the viewpoint of stably dissolving the component (A), $$Y \geq 30X - 30 \, (X \leq 4.19) \quad (1a)$$

$$Y \geq 40X - 40 \, (X \leq 3.41) \quad (1b)$$

[Component (C): Alkaline Agent]

The liquid hair dye composition of the present invention preferably further contains an alkaline agent as a component (C) to impart both good storage stability and high hair dyeability. Examples of the alkaline agent include, ammonia and salts thereof; alkanolamines such as monoethanolamine, isopropanolamine, 2-amino-2-methylpropanol, 2-aminobutanol, diethanolamine, triethanolamine, monoethanol methylamine, monoethanol dimethylamine, diethanol methylamine, monoethanol ethylamine, monoethanol diethylamine, diethanol ethylamine, monoethanol propylamine, monoethanol dipropylamine, diethanol propylamine, monoethanol butylamine, and diethanol butylamine and salts thereof; alkali metal hydroxides such as sodium hydroxide and potassium hydroxide; alkane di-amines such as 1,3-propane diamine and salts thereof; carbonates such as sodium carbonate, potassium carbonate and guanidine carbonate; and hydrogen carbonates such as sodium hydrogen carbonate and potassium hydrogen carbonate. Among these, alkanolamines and salts thereof are preferable from the viewpoint of imparting good storage stability and high hair dyeability, monoethanolamine and 2-amino-2-methylpropanol are more preferable, and among these, 2-amino-2-methylpropanol is preferable. These components (C) can be used individually or two or more components (C) can be used in combination.

The content of component (C) in the liquid hair dye composition of the present invention is preferably 0.1 mass % or more, more preferably 0.2 mass % or more, further preferably 0.25 mass % or more, and further preferably 0.5 mass % or more from the viewpoint of imparting good storage stability, and preferably 15 mass or less, more preferably 12.5 mass % or less, further preferably 10 mass % or less and further preferably 9.0 mass % or less from the viewpoint of inhibiting skin stimulation.

A direct dye other than the component (A) can be also used in combination in the liquid hair dye composition of the present invention. However, it is preferable that the content of component (A) be 1 mass or more and 100 mass % or less, furthermore 5 mass % or more and 100 mass % or less, furthermore 10 mass % or more and 100 mass % or less, and furthermore 20 mass % or more and 100 mass % or less of all dyes from the viewpoint of maintaining dyeability by the component W.

Examples of direct dyes other than the component (A) include anion dyes, cation dyes and neutral dyes. Examples of anion dyes include, Acid Black 1, Acid Blue 1, Acid Blue 3, Food Blue No. 2, Food Blue No. 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, Acid Orange 24, Acid Green 25, Solvent Green 7, Solvent Red 73, Acid Red 95, Solvent Red 43, Solvent Red 48, Acid Red 33, Solvent Violet 13, Acid Yellow 73, Food Red No. 17, Food Red No. 1, Food Yellow No. 3, Food Blue No. 2, Food Black No. 1, Food Black No. 2, Disperse Black 9, Disperse Violet 1, and alkali metal salts thereof (sodium salt and potassium salt). Examples of cation dyes include, Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12, Basic Red 22, Basic Red 76, Basic Violet 1, Basic Violet 2, Basic Violet 3, Basic Violet 10, Basic Violet 14, Basic Yellow 57, Basic Red 51, Basic Yellow 87, Basic Blue 17, and Basic Orange 31. Examples of neutral dyes including nitro dyes include, HC Blue 2, HC Blue 4, HC Blue 5, HC Blue 6, HC Blue 7, HC Blue 8, HC Blue 9, HC Blue 10, HC Blue 11, HC Blue 12, HC Blue 13, HC Brown 1, HC Brown 2, HC Green 1, HC Orange 1, HC Orange 2, HC Orange 3, HC Orange 5, HC Red BN, HC Red 1, HC Red 3, HC Red 7, HC Red 8, HC Red 9, HC Red 10, HC Red 11, HC Red 13, HC Red 54, HC Red 14, HC Violet BS, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, 2-amino-6-chloro-4-nitrophenol, picramic acid, 1,2-diamino-4-nitrobenzene, 1,4-diamino-2-nitrobenzene, 3-nitro-4-aminophenol, 1-hydroxy-2-amino-3-nitrobenzene, 2-hydroxyethylpicramic acid, 3-nitro-p-hydroxyethylaminophenol, 4-hydroxypropylamino-3-nitrophenol, and N,N-bis(2-hydroxyethyl)-2'-nitro-p-phenylenediamine.

The liquid hair dye composition of the present invention can further contain a solvent other than monoalcohol and diol. Examples of solvents other than the monoalcohol and diol include, water; at least trivalent polyols such as glycerin; N-alkylpyrrolidones such as N-methylpyrrolidone and N-ethylpyrrolidone; alkylene carbonates such as propylene carbonate; and lactones such as γ-valerolactone and γ-caprolactone. Among these, water is preferable from the viewpoint of miscibility with other agents and economic efficiency. When the liquid hair dye composition contains a solvent other than monoalcohol and diol and water, the solvent is preferably from 0 to 30 mass %, more preferably from 0 to 20 mass %, and further preferably from 0 to 10 mass % in the liquid hair dye composition.

[Surfactant]

The liquid hair dye composition of the present invention can further contain an anionic surfactant, a nonionic surfactant, an amphoteric surfactant and/or a cationic surfactant from the viewpoint of miscibility with other agents and storage stability. Cationic surfactants have the same advantages as other surfactants, and simultaneously also contribute as a conditioning component.

Examples of anionic surfactants include sulfate, sulfonate, carboxylate and phosphate type anionic surfactants. More specifically, C10-18 alkyl sulfates and ether sulfates thereof are preferable. As the alkyl ether sulfates, C12-14 alkyl ether sulfates are preferable, and lauryl ether sulfates are more preferable, and among these, one having one to four ethylene oxide group(s) in a molecule is further preferable. Examples of anionic surfactants also include fatty acid amide sulfates, and long-chain mono- and di-alkyl phosphates. Among these, alkyl sulfates are preferable, and lauryl sulfate is more preferable.

Examples of nonionic surfactants include long-chain fatty acid mono- and di-alkanolamides such as coconut fatty acid mono- or di-ethanolamide, myristic acid mono- or di-ethanolamide, stearic acid mono- or di-ethanolamide; alkyl polyglucosides having a C8-18 alkyl group and one to five glucoside unit(s); sorbitan esters such as polyethylene glycol sorbitan stearic acid, palmitic acid, myristic acid and lauric acid ester; fatty acid polyglycol esters; a polycondensate of ethylene oxide and propylene oxide commercially available under the trade name of "Pluronic (registered trademark)"; polyoxyethylene alkyl ethers (the number of carbons in the alkyl group is preferably from 10 to 22, the number of moles added of polyoxyethylene per molecule is preferably from about 2.5 to about 100, and more preferably from about 10 to about 30).

Preferable amphoteric surfactants include various known betaines such as alkyl betaines, fatty acid amido alkyl betaines, and sulfobetaines like laurylhydroxysulfobetaine, long-chain alkyl amino acids such as cocoaminoacetate, cocoaminopropionate, sodium cocoamphopropionate, and sodium cocoamphoacetate.

Examples of suitable cationic surfactants include a mono- or di-long-chain alkyl quaternary ammonium salt represented by the following general formula:

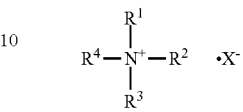

In the formula, $R^1$ represents a saturated or unsaturated linear or branched C8-22 alkyl group, or a group of $R^5CONH(CH_2)_n-$ or $R^5COO(CH_2)_n-$ ($R^5$ represents a saturated or unsaturated linear or branched C7-21 alkyl group, and n represents a number of from 1 to 4), $R^2$ represents a hydrogen atom, a saturated or unsaturated linear or branched C1-22 alkyl group, or a group of the $R^5CONH(CH_2)_n-$ or $R^5COO(CH_2)_n-$, $R^3$ and $R^4$ independently represent a hydrogen atom or a C1-4 lower alkyl group, and X represents a chloride ion, a bromide ion or a methosulfate ion.

Specific examples of the above cationic surfactant include, cetrimonium chloride, steartrimonium chloride, behentrimonium chloride, dipalmitoyl dimonium chloride, distearyl dimonium chloride, stearamidopropyl trimonium chloride, dioleoylethyl dimonium methosulfate, and dioleoylethylhydroxyethylmonium methosulfate.

The content of surfactant in the liquid hair dye composition of the present invention is preferably 0.1 mass % or more, more preferably 0.2 mass % or more, and further preferably 0.3 mass % or more from the viewpoint of imparting good storage stability, and preferably 5 mass % or less, more preferably 4 mass % or less and further preferably 2.5 mass % or less from the viewpoint of imparting good hair dyeability.

[Thickening Agent]

The liquid hair dye composition of the present invention can further contain, as a thickening agent, a synthetic polymeric compound, a semisynthetic polymeric compound or a natural polymeric compound from the viewpoint of imparting good miscibility with other agents. Examples of synthetic polymeric compounds, semisynthetic polymeric compounds and natural polymeric compounds include, (vinylpyrrolidone/dimethylaminoethyl methacrylate) copolymers (e.g., Copolymer 845, Copolymer 937, Copolymer 958; ISP Japan Ltd.), methylcellulose (e.g., METOLOSE SM; Shin-Etsu Chemical Co., Ltd.), ethyl cellulose (e.g., EMULFREE CBG; IKEDA CORPORATION), hydroxyethyl cellulose (e.g., CELLOSIZE QP4400H, QP52000H; Dow Chemical Japan, Ltd., SE-600, SE-850; Daicel Corporation), hydroxypropyl cellulose (e.g., NISSO HPC-H, HPC-M; Nippon Soda Co., Ltd.), hydroxypropyl xanthan gum (e.g., Rhaball Gum EX; Sumitomo Dainippon Pharma Co., Ltd.), pullulan (e.g., Pullulan PF-20, Pullulan PI-20; Hayashibara Co., Ltd.), and xanthan gum (e.g., Echo gum; Sumitomo Dainippon Pharma Co., Ltd.)

These thickening agents can be used individually or two or more thickening agents can be used in combination. The content of thickening agent in the liquid hair dye composition of the present invention is preferably 0.05 mass % or more, more preferably 0.1 mass % or more, and further preferably 0.5 mass % or more, and preferably 20 mass or less, more preferably 10 mass % or less, and further preferably 5 mass % or less.

[Conditioning Component]

The liquid hair dye composition of the present invention can contain a conditioning component which is suitably applied to hair. The conditioning component is usually a polymer or an oil which can be dissolved or dispersed in the liquid hair dye composition, and adheres to hair when treated with a conditioner or diluted with water or a shampoo. Examples of conditioning components include cationic polymers, silicones, higher alcohols and organic conditioning oils.

Cationic Polymer

Cationic polymers mean polymers having a cationic group or a group which can be ionized to a cationic group, and also include amphoteric polymers which are cationic as a whole. That is, examples of cationic polymers include those which have an amino group or an ammonium group on a side chain of the polymer chain, or which contain a diallyl quaternary ammonium salt as a structural unit, and for example cationized cellulose, cationic starch, cationized guar gum, a homopolymer or copolymer of a diallyl quaternary ammonium salt, and quaternized polyvinylpyrrolidone. Among these, a polymer containing a diallyl quaternary ammonium salt as a structural unit, quaternized polyvinylpyrrolidone, and cationized cellulose are preferable, and a homopolymer or copolymer of a diallyl quaternary ammonium salt and cationized cellulose are more preferable from the viewpoint of softness, smoothness and finger-combability during shampooing, hair manageability during drying, moisture retention, and storage stability of the composition.

Specific examples of cationic polymers include, dimethyl diallylammonium chloride polymers (Polyquaternium-6, e.g., MERQUAT 100; Nalco Japan Co., Ltd.), dimethyl diallylammonium chloride/acrylic acid copolymers (Polyquaternium-22, e.g., MERQUAT 280, MERQUAT 295; Nalco Japan Co., Ltd.), dimethyl diallylammonium chloride/acrylamide copolymers (Polyquaternium-7, e.g., MERQUAT 550; Nalco Japan Co., Ltd.), quaternized polyvinylpyrrolidone (Polyquaternium-11, e.g., GAFQUAT 734, GAFQUAT 755, GAFQUAT 755N; ISP Japan Ltd.), cationized cellulose (Polyquaternium-10, e.g., LEOGARD G, LEOGARD GP; Lion Corporation, Polymer JR-125, Polymer JR-400, Polymer JR-30M, Polymer LR-400, Polymer LR-30M; Dow Chemical Japan Ltd.), hydroxyethyl cellulose/dimethyl diallylammonium chloride copolymers (Polyquaternium-4, e.g., Cellcoat H-100, Cellcoat L-200; National Starch and Chemical Company).

These cationic polymers can be used individually or two or more cationic polymers can be used in combination, and the content thereof in the liquid hair dye composition is preferably 0.001 mass % or more, more preferably 0.01 mass % or more, and further preferably 0.05 mass % or more, and preferably 20 mass % or less, more preferably 10 mass % or less, and further preferably 5 mass % or less from the viewpoint of improving hair touch feel, and the storage stability of the composition.

Silicone

Examples of silicones include, dimethylpolysiloxane, modified silicone (e.g., amino-modified silicone, fluorine-modified silicone, alcohol-modified silicone, polyether-modified silicone, epoxy-modified silicone, alkyl-modified silicone, etc.), cyclic dimethylpolysiloxane, and methylphenyl polysiloxane, and dimethylpolysiloxane, polyether-modified silicone and amino-modified silicone are preferable. These silicones may include one which is diluted or dispersed in e.g., volatile silicone or non-volatile silicone, and one which is dispersed in water.

More specifically, examples thereof include, BY11-026, BY22-19, FZ-3125, SH200-1,000,000 cs (Dow Corning Toray Co., Ltd.), TSF451-100MA (Momentive Performance Materials Japan LLC) [the above are polysiloxanes], TSF4440 (Momentive Performance Materials Japan LLC), KF-6005, KF-6011 (Shin-Etsu Chemical Co., Ltd.) [the above are polyether-modified silicones], SF8451C, SF8452C, SF8457C, SM8704C (Dow Corning Toray Co., Ltd.), KF-867 (Shin-Etsu Chemical Co., Ltd.), SM8904 (Dow Corning Toray Co., Ltd.) [the above are amino-modified silicones].

These silicones can be used individually or two or more silicones can be used in combination, and the content thereof in the liquid hair dye composition is preferably 0.01 mass % or more, more preferably 0.1 mass % or more, further preferably 1.0 mass % or more, and preferably 20 mass % or less, more preferably 10 mass % or less and further preferably 5 mass % or less.

Higher Alcohol

Higher alcohols form a structure with a surfactant to prevent the separation of a hair dye composition, and moreover have an effect of improving a hair touch feel during rinsing. As higher alcohols, those which have 8 to 22 carbon atoms are preferable and those which have 16 to 22 carbon atoms are more preferable. Specific examples thereof include, cetyl alcohol, stearyl alcohol, and behenyl alcohol, and mixtures thereof.

Higher alcohols can be used individually or two or more higher alcohols can be used in combination, and the content thereof in the liquid hair dye composition is preferably 0.01 mass or more, more preferably 0.1 mass or more, and preferably 20 mass % or less, and more preferably 10 mass % or less.

Organic Conditioning Oil

The hair dye composition of the present invention preferably contains an organic conditioning oil to provide an excellent feeling of use. An organic conditioning oil which is suitably used as a conditioning component is preferably a liquid which has low viscosity and is insoluble in water. The viscosity of such organic conditioning oil measured at 40° C. is preferably 0.7 mPa·s or more, more preferably 1.0 mPa·s or more, and further preferably 2.0 mPa·s or more, and preferably 200 mPa·s or less, more preferably 100 mPa·s or less, and further preferably 50 mPa·s or less.

Examples of organic conditioning oils can include hydrocarbon oils, fatty acid esters, and mixtures thereof. The content thereof is preferably 0.01 mass % or more, more preferably 0.1 mass % or more, and preferably 20 mass % or less, and more preferably 10 mass % or less.

Hydrocarbon Oil

Examples of hydrocarbon oils include cyclic hydrocarbons, saturated or unsaturated linear aliphatic hydrocarbons, and saturated or unsaturated branched aliphatic hydrocarbons, and also include polymers and mixtures thereof. Linear hydrocarbon oils have preferably 12 to 19 carbon atoms. Branched hydrocarbon oils include hydrocarbon polymers, and have preferably above 19 carbon atoms, and also include polyolefin, which is a synthetic hydrocarbon oil. Examples of the polyolefin include polyolefin which is liquid at room temperature, more preferably liquid poly-α-olefin, and most preferably liquid hydrogenated poly-α-olefin Polyolefin used herein may be prepared by polymerizing an olefin monomer having 4 to 14 carbon atoms, preferably 6 to 12 carbon atoms.

Fatty Acid Ester

Examples of fatty acid esters include fatty acid esters having at least 10 carbon atoms. Examples of these fatty acid esters include esters having a hydrocarbon chain derived from a fatty acid and an alcohol (e.g., monoesters, polyalcohol esters, and di- and tri-carboxylic acid esters). The hydrocarbon group in these fatty acid esters may have other compatible functional groups such as an amido group and an alkoxy group as a substituent, and may be covalently bound thereto. More specifically, alkyl and alkenyl esters of fatty acid having an aliphatic chain having 10 to 22 carbon atoms, aliphatic alcohol-carboxylic acid esters having an aliphatic chain derived from alkyl and/or alkenyl alcohol having 10 to 22 carbon atoms, and mixtures thereof are suitably used.

Specific examples of preferable fatty acid esters include isopropyl isostearate, hexyl laurate, isohexyl laurate, isohexyl palmitate, isopropyl palmitate, decyl oleate, isodecyl oleate, hexadecyl stearate, decyl stearate, dihexadecyl adipate, lauryl lactate, myristyl lactate, cetyl lactate, oleyl stearate, oleyl oleate, oleyl myristate, lauryl acetate, cetyl propionate, and dioleyl adipate.

[pH]

The pH of the liquid hair dye composition of the present invention is preferably 7.5 or higher, more preferably 8.0 or higher, further preferably 8.5 or higher, and further preferably 9.0 or higher from the viewpoint of an improvement in hair dyeability, and preferably 12.0 or lower, more preferably 11.5 or lower, and further preferably 11.0 or lower from the viewpoint of inhibiting skin stimulation. In the present invention, the pH of the liquid hair dye composition means a value at 25° C. when the composition is diluted 10 times by mass with water using a pH meter (F-51 manufactured by Horiba, Ltd.)

Examples of pH adjustors to adjust a composition to the above pH include inorganic acids such as hydrochloric acid and phosphoric acid, organic acids such as citric acid, glycolic acid and lactic acid, hydrochlorides such as ammonium chloride and monoethanolamine hydrochloride, and phosphates such as potassium dihydrogen phosphate and disodium hydrogen phosphate.

[Other Optional Components]

To the liquid hair dye composition of the present invention, other components which are commonly used as cosmetic materials can be further added as long as a stable form of liquid and function as a hair dye agent are not impaired. Examples of such optional components can include, a penetration enhancer, a pearly pigment, an antiseptic agent, a sequestering agent, a stabilizing agent, an antioxidant, an ultraviolet absorbing agent, a moisturizing agent, and an odor-control agent, and specific examples of optional components include a hydrolyzed protein, a protein derivative, an amino acid, a botanical extract, a vitamin, and a perfume.

[Usage]

The liquid hair dye composition of the present invention can be used individually per se as a hair dye composition. Because the liquid hair dye composition contains a component (A) serving as a direct dye in a high concentration, the composition may be mixed with another liquid preparation before use and then the mixture can be applied to hair for hair dyeing. Here, examples of "another liquid preparation" include a diluent liquid such as an aqueous solution containing water and an alkaline agent, and moreover a shampoo, a conditioner, and a liquid hair dye composition. Examples of this hair dye composition include a one-agent type hair dye composition containing a direct dye, and a two-agent type hair dye composition containing a first agent containing an alkaline agent and an oxidation dye precursor, and a second agent containing an oxidizing agent.

In particular, when the liquid hair dye composition of the present invention is mixed with the first agent and second agent of the two-agent type hair dye composition, the central part of the section of hair is dyed with an oxidation dye and the peripheral part of the section of hair is dyed with a component (A) by applying the obtained mixed liquid to hair, and consequently hair can be dyed in two hues. On such hair dyed in two hues, a hair dyeing effect which has not been seen until now is achieved, in which the hue and color tone of hair appearance vary depending on viewing angle of the hair.

With respect to the embodiments described above, the preferred aspects of the present invention will be further disclosed below.

<1> A liquid hair dye composition comprising the following components (A) and (B), where the content (X) of the component CA) in the composition is from 1.5 to 5.16 mass %, preferably from 1.6 to 5.0 mass more preferably from 1.7 to 4.5 mass %, more preferably from 1.8 to 4.19 mass %, more preferably from 1.8 to 4.0 mass %, even more preferably from 1.8 to 3.5 mass %, even more preferably from 1.8 to 3.41 mass %, even more preferably from 1.8 to 3.0 mass %, the content (Y) of the component (B) in the composition is from 9 to 98.5 mass %, and the composition satisfies the following equation (1) (with a proviso that a composition in which the diol content is 50 mass % or more and the water content is 2 mass or less in the liquid hair dye composition is excluded).

$$Y \geq 22.75X - 22.75 \quad (1)$$

(A) an azo dye represented by the following formula (A-2)

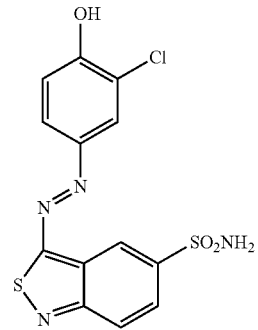

(A-2)

(B) a monoalcohol and/or diol other than alkanolamines

<2> A liquid hair dye composition comprising the following components (A) and (B), and having a pH of 7.5 or more and 12.0 or less at 25° C. when diluted with water to 10-fold by mass, where the content (X) of component (A) in the composition is from 1.5 to 5.16 mass %, the content (Y) of component (B) in the composition is from 9 to 98.5 mass %, more preferably from 10 to 97 mass %, more preferably from 12 to 95 mass %, more preferably from 14 to 93 mass %, more preferably from 16 to 90 mass %, more preferably from 20 to 85 mass %, and the composition satisfies the following equation (1) (with a proviso that a composition in which the dial content is 50 mass % or more and the water content is 2 mass % or less in the liquid hair dye composition is excluded).

$$Y \geq 22.75X - 22.75 \quad (1)$$

(A) an azo dye represented by the following formula (A-2)

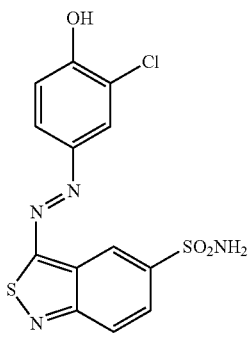

(A-2)

(B) a monoalcohol and/or a diol other than alkanolamines

<3> A liquid hair dye composition comprising the following components (A) to (C), where the content (X) of the component (A) in the composition is from 1.5 to 5.16 mass %, the total content (Y) of monoalcohol and/or a diol in the composition is from 10 to 97 mass %, preferably from 12 to 95 mass %, more preferably from 14 to 93 mass %, more preferably from 16 to 90 mass %, even more preferably from 20 to 85 mass %, and the composition satisfies the following equation (1) (with a proviso that a composition in which the diol content is 50 mass % or more and the water content is 2 mass % or less in the liquid hair dye composition is excluded).

$$Y \geq 22.75X - 22.75 \quad (1)$$

(A) an azo dye represented by the following formula (A-2)

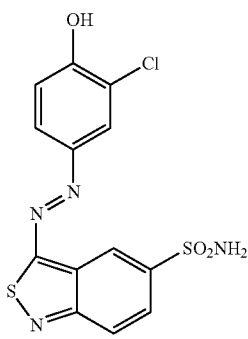

(A-2)

(B) a monoalcohol and/or a diol other than alkanolamines (C) one or more alkaline agents selected from the group consisting of an alkanolamine and a salt thereof, ammonia and a salt thereof, an alkanediamine and a salt thereof, a carbonate, a bicarbonate and an alkali metal hydroxide <4> A liquid hair dye composition comprising the following components (A) and (B), where the content (X) of the component (A) in the composition is from 1.5 to 5.16 mass %, the content (Y) of the component (B) in the composition is from 9 to 98.5 mass %, preferably from 10 to 97 mass %, more preferably from 12 to 95 mass %, more preferably from 14 to 93 mass %, more preferably from 16 to 90 mass %, more preferably from 20 to 85 mass %, and the composition satisfies the following equation (1) (with a proviso that a composition in which the diol content is 50 mass % or more and the water content is 2 mass % or less in the liquid hair dye composition is excluded).

$$Y \geq 22.75X - 22.75 \quad (1)$$

(A) an azo dye represented by the following formula (A-2)

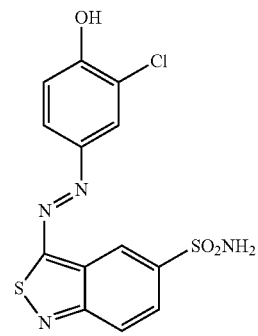

(A-2)

(B) one or more monoalcohols and/or diols selected from the group consisting of ethanol, 1-propanol, 2-propanol, benzyl alcohol, 2-benzyloxyethanol, ethoxyethanol, ethoxy diglycol, methoxyethanol, propylene glycol, 1,3-butanediol, polyethylene glycol and diethylene glycol <5> A liquid hair dye composition comprising the following components (A) to (D), where the content (X) of the component (A) in the composition is from 1.5 to 5.16 mass %, the total content (Y) of the monoalcohol and/or diol in the composition is from 10 to 97 mass %, preferably from 12 to 95 mass %, more preferably from 14 to 93 mass %, more preferably from 16 to 90 mass %, even more preferably from 20 to 85 mass %, and the composition satisfies the following equation (1) (with a proviso that a composition in which the diol content is 50 mass % or more and the water content is 2 mass % or less in the liquid hair dye composition is excluded).

$$Y \geq 22.75X - 22.75 \quad (1)$$

(A) an azo dye represented by the following formula (A-2)

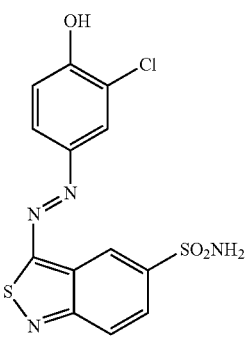

(A-2)

(B) a monoalcohol and/or a diol other than alkanolamines
(C) an alkaline agent
(D) one or more species selected from the group consisting of a surfactant, a thickener and a conditioning agent
<6> The liquid hair dye composition according to any one of <1> to <5>, comprising water as a solvent other than the component (B).
<7> A liquid hair dye composition comprising the following components (A) to (C), where
the content (X) of component (A) in the composition is from 1.5 to 5.16 mass %,
the content (Y) of component (B) in the composition, is from 9 to 98.5 mass %,
the content of component (C) in the composition is from 0.1 to 15 mass %,
the composition satisfies the following equation (1) (with a proviso that a composition in which the diol content is 50 mass % or more and the water content is 2 mass % or less in the liquid hair dye composition is excluded).

$$Y \geq 22.75X - 22.75 \tag{1}$$

(A) an azo dye represented by the following formula (A-2)

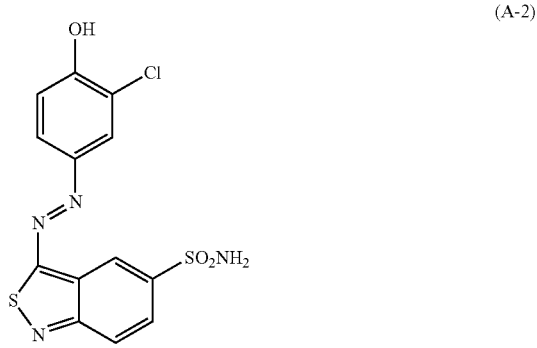 [SMILES: NS(=O)(=O)c1ccc2nsc(/N=N/c3ccc(O)c(Cl)c3)c2c1]

(B) a monoalcohol and/or a diol other than alkanolamines
(C) an alkaline agent
<8> The liquid hair dye composition according to <7>, where the content (X) of the component (A) is from 1.6 to 5.0 mass %.
<9> The liquid hair dye composition according to <7>, where the content (X) of the component (A) is from 1.7 to 4.5 mass %.
<10> The liquid hair dye composition according to <7>, where the content (X) of the component (A) is from 1.8 to 4.19 mass %.
<11> The liquid hair dye composition according to <7>, where the content (X) of the component (A) is from 1.8 to 4.0 mass %.
<12> The liquid hair dye composition according to any one of <7> to <11>, where the content (Y) of the component (B) is from 10 to 97 mass %.
<13> The liquid hair dye composition according to any one of <7> to <11>, where the content (Y) of the component (B) is from 12 to 95 mass %.
<14> The liquid hair dye composition according to any one of <7> to <11>, where the content (Y) of the component (B) is from 14 to 93 mass %.
<15> The liquid hair dye composition according to any one of <7> to <11>, where the content (Y) of the component (B) is from 16 to 90 mass %.
<16> The liquid hair dye composition according to any one of <7> to <11>, where the content (Y) of the component (B) is from 20 to 85 mass %.
<17> The liquid hair dye composition according to any one of <7> to <16>, where the content of the component (C) is from 0.2 to 12.5 mass %.
<18> The liquid hair dye composition according to any one of <7> to <16>, where the content of the component (C) is from 0.25 to 10 mass %.
<19> The liquid hair dye composition according to any one of <7> to <16>, where the content of the component (C) is from 0.5 to 9.0 mass %.
<20> The liquid hair dye composition according to any one of <7> to <19>, where the component (B) comprises one or more species selected from the group consisting of a lower monoalcohol having 2 or 3 carbon atoms, a monocyclic aromatic monoalcohol, and a diol having 2 to 6 carbon atoms.
<21> The liquid hair dye composition according to any one of <7> to <19>, where the component (B) contains one or more species selected from the group consisting of a monocyclic aromatic monoalcohol and a diol having 2 to 6 carbon atoms.
<22> The liquid hair dye composition according to any one of <7> to <19>, where the component (B) contains one or more species selected from diols having 2 to 6 carbon atoms.
<23> The liquid hair dye composition according to any one of <7> to <19>, where the component (B) comprises one or more species selected from the group consisting of ethanol, 1-propanol, 2-propanol, benzyl alcohol, 2-benzyloxyethanol, propylene glycol, 1,3-butanediol, and diethylene glycol.
<24> The liquid hair dye composition according to any one of <7> to <19>, where the component (B) comprises one or more species selected from the group consisting of benzyl alcohol, 2-benzyloxyethanol, propylene glycol, 1,3-butanediol, and diethylene glycol.
<25> The liquid hair dye composition according to any one of <7> to <19>, where the component (B) comprises one or more species selected from the group consisting of propylene glycol, 1,3-butanediol, and diethylene glycol.
<26> The liquid hair dye composition according to any one of <7> to <19>, where the component (B) comprises propylene glycol.
<27> The liquid hair dye composition according to any one of <7> to <26>, where the component (C) comprises an alkanolamine or a salt thereof.
<28> The liquid hair dye composition according to any one of <7> to <26>, where the component (C) comprises one or two species selected from the group consisting of monoethanolamine and 2-amino 2-methylpropanol.
<29> The liquid hair dye composition according to any one of <7> to <26>, where the component (C) comprises 2-amino-2-methylpropanol.
<30> The liquid hair dye composition according to any one of <7> to <29>, where the pH at 25° C. when diluted with water to 10-fold by mass is 8.0 or more and 12.0 or less.
<31> The liquid hair dye composition according to any one of <7> to <29>, where the pH at 25° C. when diluted with water to 10-fold by mass is 8.5 or more and 11.5 or less.
<32> The liquid hair dye composition according to any one of <7> to <29>, where the pH at 25° C. when diluted with water to 10-fold by mass is 9.0 or more and 11.0 or less.
<33> A liquid hair dye composition containing the following components (A) to (C), where
the content (X) of component (A) in the composition is from 1.6 to 5.0 mass %, the content (Y) of the component (B) in the composition is from 20 to 85 mass %, the content of the component (C) in the composition is from 0.5 to 9.0 mass %, the pH at 25° C. when diluted with water to 10-fold is 7.5 or more and 12.0 or less, and the composition satisfies the following equation (1) (with a proviso that a composition in which the diol content is 50 mass % or more and the water content is 2 mass % or less in the liquid hair dye composition is excluded).

$$Y \geq 22.75X - 22.75 \quad (1)$$

(A) an azo dye represented by the following formula (A-2)

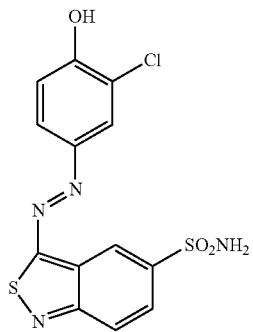

(A-2)

(B) a monoalcohol and/or a diol other than alkanolamines, containing one or more species selected from the group consisting of propylene glycol, 1,3-butanediol and diethylene glycol (C) an alkaline agent comprising one or two species selected from the group consisting of monoethanolamine and 2-amino-2-methylpropanol <34> A method for dyeing hair by applying to hair a mixture obtained after mixing a liquid hair dye composition according to any one of <7> to <33> and another liquid preparation before use.

<35> The hair dyeing method according to <34>, where the other liquid formulation is a hair dye composition.

<36> The hair dyeing method according to <34>, where the other liquid formulation is a two-agent type hair dye composition consisting of a first agent comprising an alkaline agent and an oxidation dye precursor, and a second agent comprising an oxidizing agent.

EXAMPLES

Examples 1 to 5 and Comparative Examples 1 to 5

A concentrated dye liquid composition was prepared by mixing components shown in Tables 1 and 2, and the storage stability of each concentrated dye liquid composition was evaluated in accordance with the following method.

[Method for Evaluating Storage Stability of Composition]

A prepared concentrated dye liquid composition was left to stand at 30° C. for 6 days, and then observed visually and microscopically, and storage stability was evaluated by the following criteria, A: totally uniformly dissolved, transparent, and no deposits observed, B: opaque, having fine insoluble matter, and uniformly dispersed, and C: insoluble matter or deposits observed.

In addition, a first agent and a second agent of an oxidation hair dye agent having composition shown in Table 3 were prepared. Hair was dyed using each dye concentrated liquid composition shown in Table 1 and the oxidation hair dye agent in accordance with the following hair dyeing method. The miscibility, hair touch feel during rinsing, uniform dyeability, and effect of changing the hue and color tone of hair appearance depending on viewing angle of the hair were evaluated.

<Hair Dyeing Method>

A hair tress with a length of 15 cm and a weight of about 1 g was created using white hair purchased from IHIP, and used for evaluation.

In a plastic beaker, 4 g of first agent, 6 g of second agent and 1.25 g of dye concentrated solution were taken, and the obtained mixture was mixed ten times with a spatula. To evaluation hair, about 1 g of this mixed liquid was applied with a brush, and the hair was left to stand at 30° C. for 30 minutes to dye hair. The hair was rinsed with 40° C. hot water for 30 seconds or more, washed with a shampoo, treated with a conditioner and then dried.

[Method for Evaluating Miscibility of Composition]

A mixed liquid obtained by mixing a first agent, a second agent and a dye concentrated solution in the hair dyeing method was observed, and miscibility was evaluated by criteria described below, A: easily uniformly mixed, and no insoluble matter observed, B: uniformly mixed, but requiring time until dissolution, and C: not uniformly mixed, and insoluble matter observed.

[Method for Evaluating Hair Touch Feel During Rinse]

Hair softness when bent in 40° C. hot water during rinsing was evaluated in a sensory manner. The softness of a hair tress was evaluated by feeling resistance when the hair tress is wound around a finger in hot water. Evaluation was made by five evaluators using untreated hair as the standard on a scale of 1 to 5 described below, and the average of five expert panelists was shown as a score in Table 1, 1: feeling softer than untreated hair, 2: feeling slightly softer than untreated hair, 3: equal to untreated hair, 4: feeling slightly harder than untreated hair, and 5: feeling harder than untreated hair.

[Method for Evaluating Uniform Dyeability]

Different three points on dried hair (each one point in the central part of each region obtained by dividing hair into 3 portions in the length direction) were measured using a Chroma Meter (CR-400 manufactured by Konica Minolta, Inc.) by the CIE calorimetric system (L*,a*,b*), and a color difference (□E*) between respective measurement points was calculated. That is, when respective measurement points were considered as A, B and C, color differences between A and B, A and C, and B and C were calculated. The greatest one of color differences between A and B, A and C, and B and C was evaluated as color unevenness.

$$\Delta E^* = \sqrt{(L_1^* - L_0^*)^2 + (a_1^* - a_0^*)^2 + (b_1^* - b_0^*)^2}$$

[where, $L^*_0$, $a^*_0$ and $b^*_0$ represent values of $L^*$, $a^*$ and $b^*$, respectively, on a measurement point, and $L^*_1$, $a^*_1$ and $b^*_1$ represent values of $L^*$, $a^*$ and $b^*$ of hair immediately after hair dyeing on a point different from the above measurement point.]

[Method for Evaluating Changes in Hue and Color Tone of Hair Appearance Depending on Viewing Angle of the Hair]

Dried hair after hair dyeing was observed as a hair tress at a distance of about 30 cm under an artificial solar lighting manufactured by Serb Ltd. (model XC-100 AP, 100 W). An evaluator fixed one end of an evaluation hair tress and moved another end to change hair angles, and observed changes in hair color.

The degree of color changes was evaluated by five evaluators using a non-restrictive close-ended system of a direct evaluation method. That is, a 10 cm-long straight line was drawn horizontally and the left and right ends of the straight line were defined as "not feeling color changes at all even when changing angles" and "seeing entirely different color depending on viewing angle" respectively. A position, shown in cm, from the left end of the straight line of hair in Examples and Comparative Examples was investigated and shown. The average of the five evaluators was shown as a score in Table 1.

TABLE 1

| | | | Example | | | | Comparative Example | | |
|---|---|---|---|---|---|---|---|---|---|
| | | | 1 | 2 | 3 | 4 | 1 | 2 | 3 |
| Compositions (mass %) | (A) | (A-2) HC Blue 18 | 3.0 | 2.0 | 4.0 | 4.0 | 2.0 | 4.0 | 0.4 |
| | (B) | Propylene Glycol | 46.5 | 23.5 | 69.0 | — | 20.0 | 64.0 | 7.0 |
| | | Benzyl alcohol | — | — | — | 70.0 | — | — | — |
| | Alkaline agent | 2-Amino-2-methyl-1-propanol | 4.0 | 4.0 | 4.0 | 4.0 | 4.0 | 4.0 | 4.0 |
| | Other solvent | Water | 46.5 | 70.5 | 23.0 | 22.0 | 74.0 | 28.0 | 88.6 |
| | | Total | 100.0 | 100.0 | 100.0 | 100.0 | 100.0 | 100.0 | 100.0 |
| pH (10-fold dilution with water) | | | 10.4 | 10.8 | 10.3 | 10.3 | 10.5 | 10.1 | 11.1 |
| Evaluation | Storage stability | | A | A | A | B | C | C | A |
| | Miscibility | | A | A | A | A | C | C | A |
| | Feel (softness during rinsing) | | 1.4 | 1.6 | 1.2 | 1.4 | 2.6 | 3.8 | 3.0 |
| | Uniform dyeability (ΔE *) | | 2.7 | 2.4 | 2.5 | 2.5 | 4.9 | 9.2 | 2.2 |
| | Changes in the hue and tone of the appearance of the hair depending on the angle at which the hair is viewed | | 7.7 | 7.0 | 7.9 | 4.9 | 3.9 | 4.4 | 1.9 |

TABLE 2

| | | | Example | Comparative Example | |
|---|---|---|---|---|---|
| | | | 5 | 4 | 5 |
| Compositions (mass %) | (A) | (A-2) HC Blue 18 | 2.0 | 2.0 | 4.0 |
| | (B) | Benzyl alcohol | 30.0 | 10.0 | 50.0 |
| | Alkaline agent | 2-Amino-2-methyl-1-propanol | 4.0 | 4.0 | 4.0 |
| | Other solvent | Water | 64.0 | 84.0 | 42.0 |
| | | Total | 100.0 | 100.0 | 100.0 |
| pH (10-fold dilution with water) | | | 10.7 | 10.6 | 10.5 |
| Evaluation | Storage stability | | B | C | C |

TABLE 3

| | | (mass %) |
|---|---|---|
| First agent | p-Aminophenol | 0.31 |
| | 2,4-Diaminophenoxyethanol hydrochloride | 0.53 |
| | Ascorbic acid | 0.15 |
| | Anhydrous sodium sulfite | 0.20 |
| | Ammonia water (28 mass %) | 6.00 |
| | EDTA·4Na | 0.05 |
| | Purified Water | 92.76 |
| | Total first agent | 100.00 |
| Second agent | Hydrogen peroxide (35%) | 5.80 |
| | Purified Water | 94.20 |
| | Total second agent | 100.00 |

The invention claimed is:

1. A liquid hair dye composition, comprising:
(A) an azo dye represented by the formula (A-2):

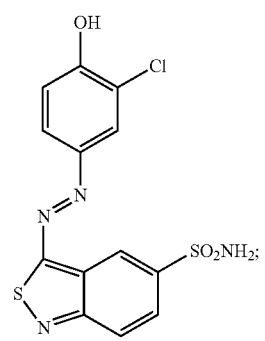

(A-2)

and (B) at least one selected from the group consisting of a lower monoalcohol having 2 or 3 carbon atoms, a monocyclic aromatic monoalcohol, and a diol having 2 to 6 carbon atoms,
wherein
a content (X) of the component (A) in the composition is 1.5 mass % or more and 5.16 mass % or less,
a content (Y) of the component (B) in the composition is 9 mass % or more and 98.5 mass % or less, and
the composition satisfies the equation (1): Y≥22.75X−22.75 (1),
with a proviso that that the composition is not a composition in which a diol content is 50 mass % or more and a water content is 2 mass % or less.

2. The liquid hair dye composition according to claim 1, further comprising an alkaline agent.

3. The liquid hair dye composition according to claim 2, wherein the alkaline agent is one or more of an alkanolamine and a salt thereof, ammonia and a salt thereof, an alkanediamine and a salt thereof, a carbonate, a hydrogen carbonate, and an alkali metal hydroxide.

4. The liquid hair dye composition according to claim 1, having a pH of 7.5 or more and 12.0 or less at 25° C. when diluted with water to 10-fold by mass.

5. The liquid hair dye composition according to claim 1, which is suitable to be mixed with another liquid preparation before use.

6. The liquid hair dye composition according to claim 5, wherein the other liquid preparation is a hair dye composition.

7. The liquid hair dye composition according to claim 5, wherein the other liquid preparation is a two-agent type hair dye composition consisting of a first agent comprising an alkaline agent and an oxidative dye precursor and a second agent comprising an oxidizing agent.

8. The liquid hair dye composition according to claim 5, wherein the other liquid preparation is a multiple-agent type hair dye composition comprising a first agent comprising an alkaline agent and an oxidation dye precursor, and a second agent comprising an oxidizing agent.

9. A method for dyeing hair, comprising:
mixing a liquid hair dye composition comprising (A) an azo dye represented by the formula (A-2) and (B) at least one selected from the group consisting of a lower monoalcohol having 2 or 3 carbon atoms, a monocyclic aromatic monoalcohol, and a diol having 2 to 6 carbon atoms, with another liquid preparation to prepare a mixture:

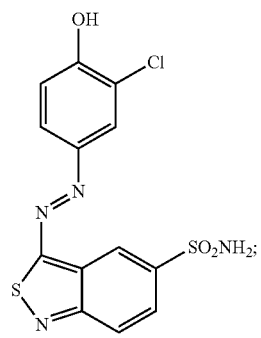

(A-2)

and subsequently
applying the mixture to hair for dyeing the hair,
wherein
a content (X) of the component (A) in the composition is 1.5 mass % or more and 5.16 mass % or less,
a content (Y) of the component (B) in the composition is 9 mass % or more and 98.5 mass % or less, and
the liquid hair dye composition satisfies the equation (1):

$$Y > 22.75X - 22.75 \qquad (1),$$

with a proviso that the liquid hair dye composition is not a composition in which a diol content is 50 mass % or more and a water content is 2 mass % or less.

10. The method according to claim 9, wherein the other liquid preparation is a hair dye composition.

11. The method according to claim 9, wherein the other liquid preparation is a multiple-agent type hair dye composition comprising a first agent comprising an alkaline agent and an oxidation dye precursor, and a second agent comprising an oxidizing agent.

12. The method according to claim 9, wherein the other liquid preparation is a two-agent type hair dye composition consisting of a first agent comprising an alkaline agent and an oxidation dye precursor, and a second agent comprising an oxidizing agent.

* * * * *